US009579122B2

(12) United States Patent
Ross et al.

(10) Patent No.: US 9,579,122 B2
(45) Date of Patent: Feb. 28, 2017

(54) COLLAPSIBLE FIXATOR SYSTEM

(71) Applicant: TEXAS SCOTTISH RITE HOSPITAL FOR CHILDREN, Dallas, TX (US)

(72) Inventors: John David Ross, Ovilla, TX (US); Mikhail L. Samchukov, Coppell, TX (US); Alexander M. Cherkashin, Flower Mound, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 0 days.

(21) Appl. No.: 14/325,227

(22) Filed: Jul. 7, 2014

(65) Prior Publication Data

US 2016/0000465 A1    Jan. 7, 2016

(51) Int. Cl.
  *A61B 17/62* (2006.01)
  *A61B 19/00* (2006.01)

(52) U.S. Cl.
  CPC .............. *A61B 17/62* (2013.01); *A61B 19/54* (2013.01)

(58) Field of Classification Search
  CPC ......... A61B 17/62; A61B 17/66; A61B 17/60; A61B 17/6466; A61B 17/6416; A61B 17/645; A61B 17/6441; A61B 17/6458; A61B 17/6425; A61B 17/8875; A61B 17/1739; A61B 17/484; A61B 17/84; A61B 17/663; A61B 17/6475; A61B 17/7077; A61B 2017/292

(Continued)

(56) References Cited

U.S. PATENT DOCUMENTS 1,257,297 A    2/1918    Brown
2,250,417 A    7/1941    Ettinger
(Continued)

FOREIGN PATENT DOCUMENTS

GB    2031731    *   4/1980    ............ A61B 90/39
GB    2031731 A        4/1980
(Continued)

OTHER PUBLICATIONS

International Search Report and Written Opinion, PCT/IB2015/054666, dated Sep. 16, 2015, 10 pages.

*Primary Examiner* — Pedro Philogene
(74) *Attorney, Agent, or Firm* — Baker & McKenzie LLP

(57) ABSTRACT

A collapsible fixator system comprising a first frame member and a second frame member and at least one strut. Each frame member comprises an upper surface, a lower surface, and a plurality of apertures extending from the upper surface to the lower surface. Each of the at least one struts comprises first and second strut connectors, such that the first and the second strut connectors are operable to releasably connect the strut to the first frame member and the second frame member. When the first and second strut connectors are in a first, collapsed position, the strut is releasably positioned substantially parallel to the upper and lower surfaces of the first and second frame members. When the first and second strut connectors are in a second, erect position, the strut may be fixedly positioned such that the first and second frame members are spaced apart from one another.

24 Claims, 15 Drawing Sheets

(58) Field of Classification Search
USPC .................................................. 606/54–59
See application file for complete search history.

(56) References Cited

U.S. PATENT DOCUMENTS

| | | | |
|---|---|---|---|
| 2,346,346 A | | 4/1944 | Anderson |
| 4,392,487 A | | 7/1983 | Selner et al. |
| 4,708,131 A | | 11/1987 | Kendrick |
| 4,865,023 A | | 9/1989 | Craythorne et al. |
| 4,955,370 A | | 9/1990 | Pettine |
| 5,407,420 A | | 4/1995 | Bastyr et al. |
| 5,429,637 A | | 7/1995 | Hardy |
| 5,451,225 A | | 9/1995 | Ross, Jr. et al. |
| 5,702,389 A | * | 12/1997 | Taylor .................. A61B 17/62 606/56 |
| 5,728,095 A | | 3/1998 | Taylor et al. |
| 5,931,837 A | | 8/1999 | Marsh et al. |
| 6,461,358 B1 | | 10/2002 | Faccioli et al. |
| 7,044,926 B2 | | 5/2006 | Carlson |
| 7,182,743 B2 | | 2/2007 | Slautterback et al. |
| 7,306,601 B2 | * | 12/2007 | McGrath ............... A61B 17/62 606/53 |
| 7,507,215 B2 | | 3/2009 | Ryan |
| 7,931,650 B2 | | 4/2011 | Winquist et al. |
| 8,333,766 B2 | | 12/2012 | Edelhauser et al. |
| 8,382,755 B2 | | 2/2013 | Austin et al. |
| 8,679,117 B2 | | 3/2014 | Knuchel et al. |
| 8,727,972 B2 | | 5/2014 | Zhang et al. |
| 9,044,271 B2 | | 6/2015 | Edelhauser et al. |
| 2003/0191466 A1 | * | 10/2003 | Austin ................... A61B 17/62 606/54 |
| 2007/0055234 A1 | * | 3/2007 | McGrath ............... A61B 17/62 606/56 |
| 2011/0313419 A1 | | 12/2011 | Mullaney |
| 2012/0143190 A1 | * | 6/2012 | Wolfson ................ A61B 17/64 606/56 |

FOREIGN PATENT DOCUMENTS

| | | | | |
|---|---|---|---|---|
| WO | 00/03647 A1 | | 1/2000 | |
| WO | WO0003647 | * | 1/2000 | ............ A61B 90/39 |
| WO | 2010/104567 A1 | | 9/2010 | |

* cited by examiner

COLLAPSIBLE FIXATOR SYSTEM

TECHNICAL FIELD

The present disclosure relates to external orthopedic fixation systems, and more particularly to collapsible fixator systems.

BACKGROUND

External orthopedic fixation devices are commonly used in the treatment of limb injuries and deformations including skeletal fractures, soft tissue injuries, delayed union of skeletal bones resulting from slow healing, non-union of skeletal bones involving unhealed bones, mal-union of bones resulting from the improper healing of broken or fractured bones, congenital deformities resulting from bones developing in a mal-position, and bone widening or twisting. Medical procedures involving external orthopedic fixation devices include limb lengthening, deformity correction, and the treatment of fractures, mal-unions, non-unions, and bone defects. Typically, external fixator systems may be placed on a subject's (e.g., a human or another vertebrate animal) affected limb by a medical professional to set the impacted bones or bone fragments in a desired position. The fixator systems may be adjusted throughout the treatment process in order to set and maintain the bones in a desired position. However, the known fixator systems are often large and unwieldy, making it difficult to transport, store, and then affix to a subject.

Therefore, it is desirable to have an external fixator system that may be readily collapsed or erected to allow the system to be more easily fitted to a patient's limb and for adjustment of the fixator system without the need to remove the system from the patient's limb.

BRIEF SUMMARY

Disclosed herein is a collapsible fixator system and related methods of collapsing or erecting the collapsible fixator system. The collapsible fixator system may comprise a first frame member and a second frame member and at least one strut. Each frame member may comprise an upper surface, a lower surface, and a plurality of apertures extending from the upper surface to the lower surface. The first frame member and the second frame member may be substantially U-shaped and may each comprise a first arm, a second arm, and a connecting portion defined there between.

Each of the at least one struts may comprise a first strut connector disposed on a first end of the strut and a second strut connector disposed on a second end of the strut, such that the first strut connector is operable to releasably connect the first end of the strut to the first frame member at a first aperture and the second strut connector is operable to releasably connect the second end of the strut to second frame member at a second aperture. When the first and second strut connectors are in a first, collapsed position, the strut is releasably positioned substantially parallel to the upper and lower surfaces of the first and second frame members. When the first and second strut connectors are in a second, erect position, the strut may be fixedly positioned substantially perpendicular to the upper and lower surfaces of the first and second frame members.

Each of the plurality of apertures may comprise an upper and a lower portion with the upper portion comprising a recessed area defined within the upper surface of the frame member and operable to receive a hemispherical feature of a strut. The lower portion of the aperture may comprise a leveled region substantially parallel to and defined within the lower surface of the frame member and operable to interact with the first or the second strut connector. The lower portion may further comprise an inclined region operable to interact with the first or the second strut connector, with the inclined region gradually sloping from an outer surface of the frame member to the leveled region. When a strut connector is in the first position, the strut connector may be adjacent to the inclined region of the aperture. When a strut connector is in the second position, the strut connector may be adjacent to the leveled region of the aperture.

The at least one strut of a collapsible fixator system may further comprise a body positioned between the first strut connector and the second strut connector. The at least one strut may further comprise a first hemispherical feature positioned between the body and the first strut connector, and a second hemispherical feature positioned between the body and the second strut connector. The first hemispherical feature may be operable to rotate within an upper portion of the first aperture such that the first strut connector reversibly transitions between the first and second positions. The second hemispherical feature may be operable to rotate within an upper portion of the second aperture such that the second strut connector reversibly transitions between the first and second positions.

The at least one strut may further comprise a first rotational joint member positioned between the body and the first strut connector, and a second rotational joint member positioned between the body and the second strut connector. The first rotational joint member may be operable to rotate the first strut connector and the body relative to one another, and the second rotational joint member may be operable to rotate the second strut connector and the body relative to one another.

BRIEF DESCRIPTION OF THE DRAWINGS

Embodiments are illustrated by way of example in the accompanying figures, in which like reference numbers indicate similar parts, and in which.

DETAILED DESCRIPTION

Figure 1:
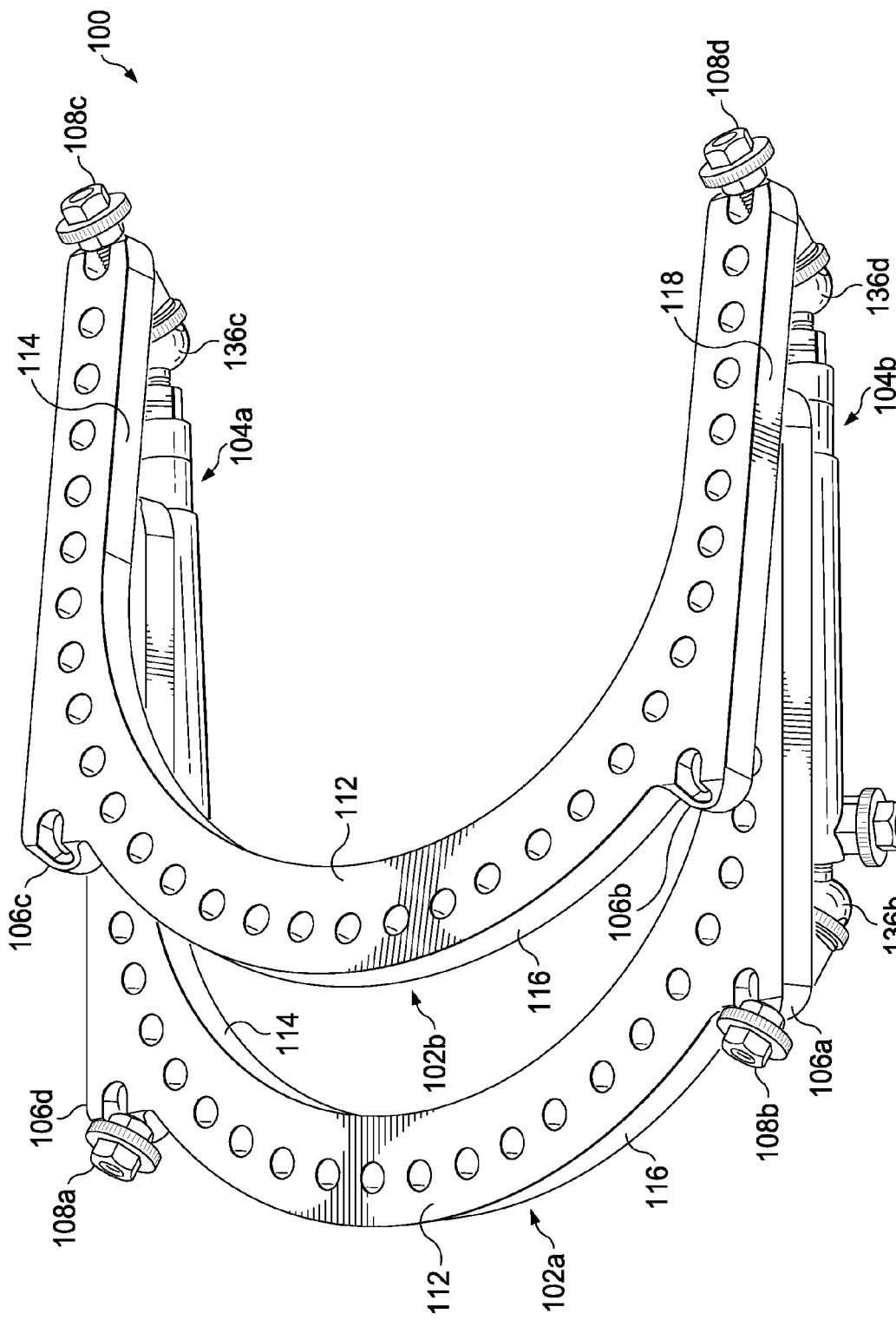
FIG. 1 illustrates an isometric view of a collapsible fixator system depicting two struts connected to two frame members in a first, collapsed position, in accordance with one embodiment of the present disclosure.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an", and "the" are not intended to refer to only a singular entity, but include the general class of which a specific example may be used for illustration. The terminology herein is used to describe specific embodiments of the disclosure, but their usage does not limit the disclosure, except as outlined in the claims.

The present disclosure relates generally to a collapsible fixator system. The collapsible fixator system may comprise a first frame member and a second frame member and at least one strut. The collapsible fixator system may be readily collapsed or erected to allow the system to be more easily fitted to a patient's limb and for adjustment of the fixator system without the need to remove the system from the patient's limb. The collapsible fixator system may be readily transportable to emergency response locations and may be temporarily fixed to a subject (e.g., a human or another vertebrate animal) during transport to the medical care facility. Additionally, the collapsible fixator system may be applied as a semi-permanent or permanent external orthopedic fixation device. The collapsible fixation system may be sterilized in situ or provided in a sterile pre-packaged kit.

The methods of the present disclosure may be performed with a subject (e.g., a human or another vertebrate animal). One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

A collapsible fixator system may be constructed along and at least partially surrounding the selected bone(s). The collapsible fixation device may include a plurality of frame members (e.g. U-shaped, substantially ring shaped, an oval shape, a partial ring shape, or a plate shape) fixed in position relative to one another by numerous connecting rods or struts secured to the frame members.

The collapsible fixation system may be connected to the selected bone(s). Connection may be performed at any suitable time, such as before, during, and/or after construction of the collapsible fixation device. For example, the collapsible fixation device may be assembled and then connected to bone, or individual collapsible fixation device members or collapsible fixation device sub-assemblies may be connected to the bone before the collapsible fixation device is fully assembled. Connection of the collapsible fixation device to bone may include placing connectors, such as wires, pins, screws, and/or rods, among others through the skin and into, through, and/or around the selected bone.

It is contemplated that any embodiment discussed in this specification can be implemented with respect to any method, kit, or device of the disclosure, and vice versa. Furthermore, devices taught herein can be used to achieve methods of the disclosure.

One or more components of the collapsible fixator frame and strut system disclosed herein may be made from any of the following materials: (a) any biocompatible material (which biocompatible material may be treated to permit bone ingrowth or prohibit bone ingrowth); (b) a plastic; (c) a wood; (d) a fiber; (e) a polymer (e.g. polypropylene, polystyrene, polyurethane, latex, nylon; (f) a metal (e.g., a pure metal such as titanium, chromium, or copper and/or an alloy such as Ti-Al-Nb, TI-6Al-4V, stainless steel, bronze); (g) a radioluscent material (e.g., carbon fiber PEEK or aluminum); (h) a ceramic; (i) a rubber) or (j) any combination thereof. Furthermore, one or more components of the collapsible fixator frame and strut system may be varied in size for use by both pediatric and adult patients.

Figure 2A:
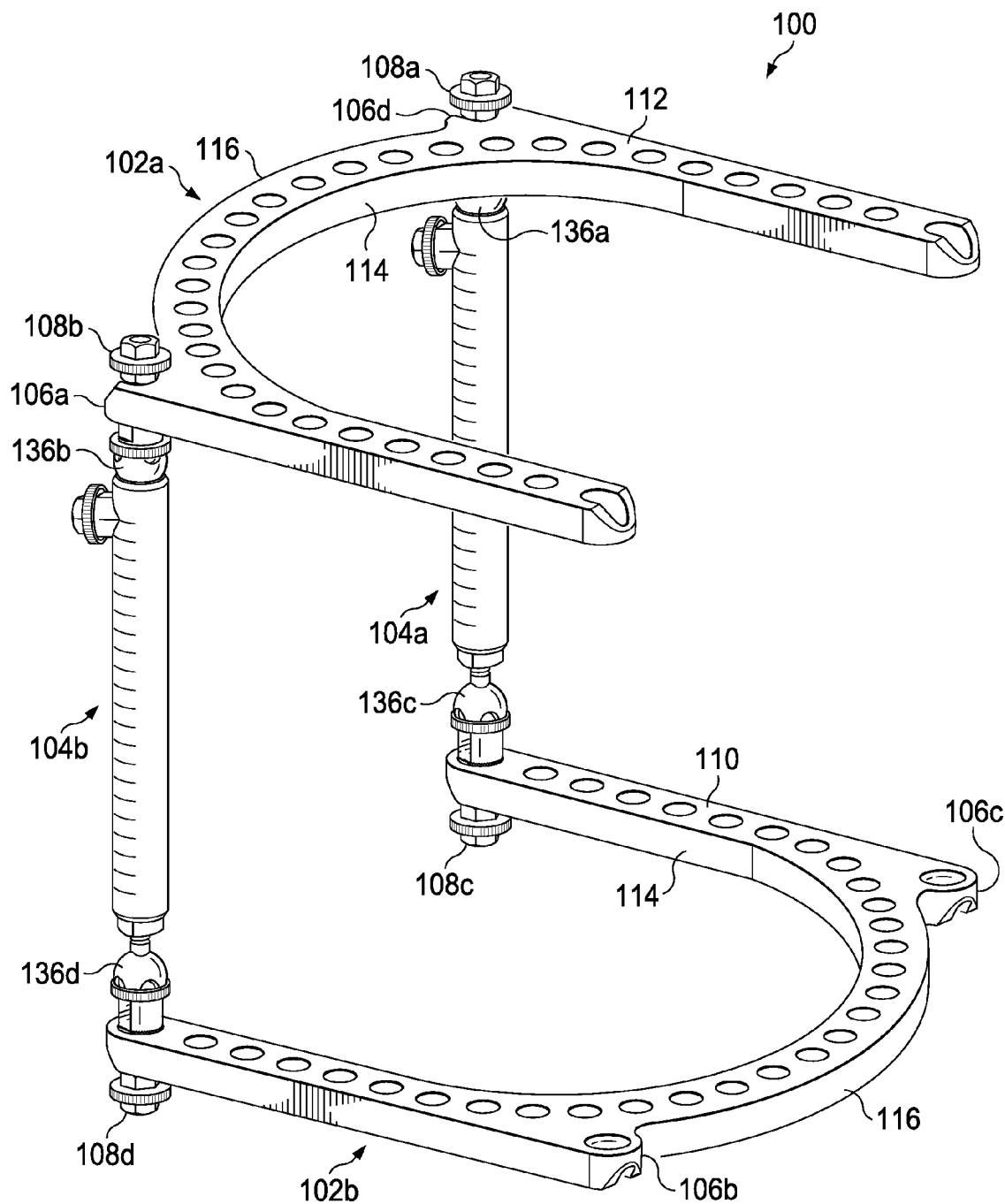
FIG. 2A illustrates an isometric view of the collapsible fixator system of FIG. 1 depicting two struts connected to two frame members in a second, erect position, in accordance with one embodiment of the present disclosure.
Figure 2B:
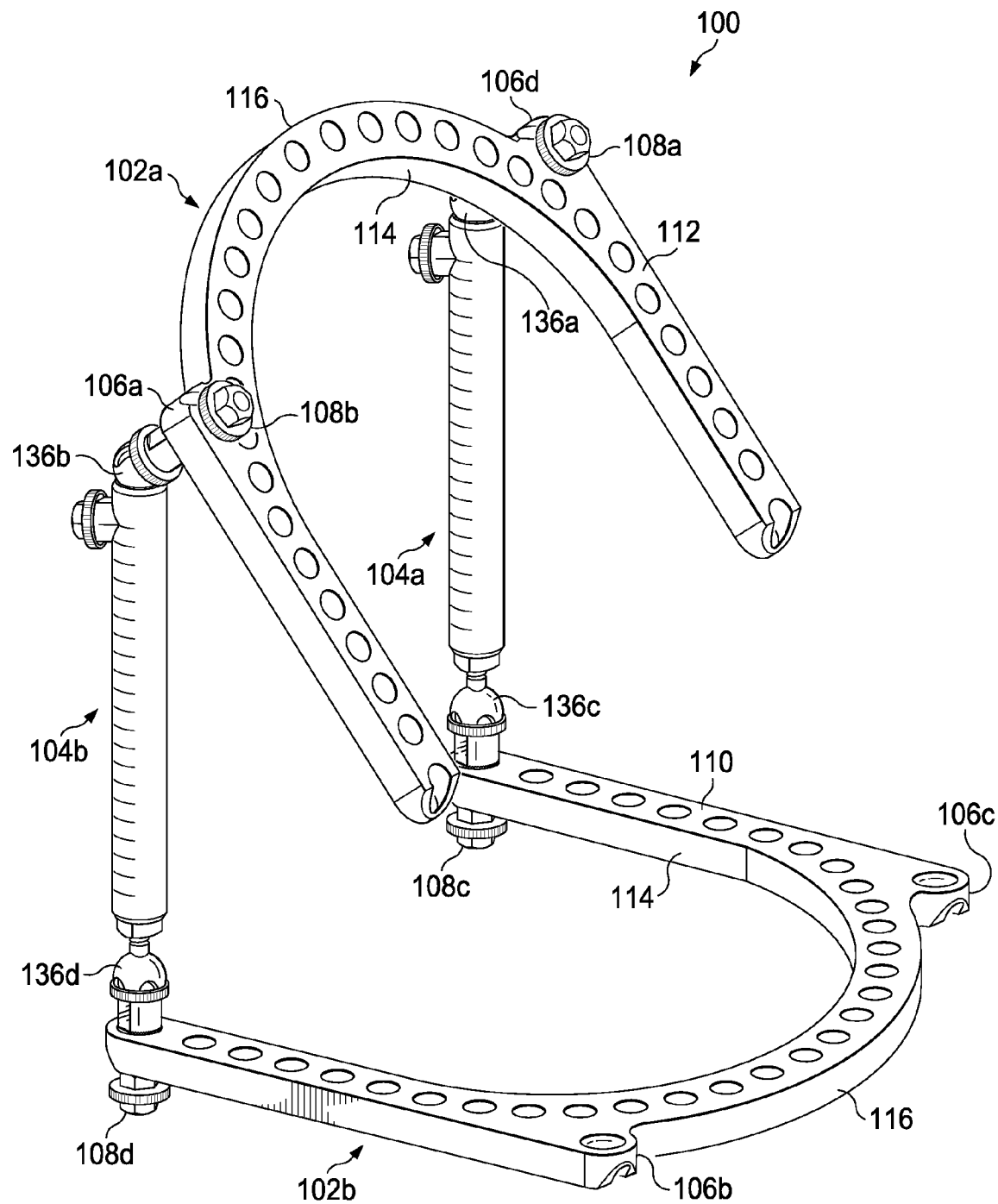
FIG. 2B illustrates an isometric view of the collapsible fixator system of FIG. 1 depicting two struts connected to two frame members in a second, erect position, in accordance with one embodiment of the present disclosure.

FIG. 1 illustrates an isometric view of a collapsible fixator system 100 depicting two struts connected to two frame members in a first, collapsed position, in accordance with one embodiment of the present disclosure. FIG. 2A illustrates an elevational view of the collapsible fixator system 100 of FIG. 1 depicting two struts connected to two frame members in a second, erect position, in accordance with one embodiment of the present disclosure. FIG. 2B illustrates an elevational view of the collapsible fixator system 100 of FIG. 1 depicting two struts connected to two frame members in a second, erect position, in accordance with one embodiment of the present disclosure.

As shown in FIGS. 1, 2A, and 2B, the collapsible fixator system 100 may comprise a first frame member 102a, a second frame member 102b, a first strut 104a, and a second strut 104b. The first frame member 102a and the second frame member 102b may each have an upper surface 110, a lower surface 112, an inner surface 114, and an outer surface 116. The upper surfaces 110 and the lower surfaces 112 may be relative to the first frame member 102a and the second frame member 102b when the collapsible fixator system is in the second, erect position, as shown in FIGS. 2A and 2B. The first frame member 102a may comprise a first protruding portion 106a and a second protruding portion 106d. The second frame member 102b may comprise a first protruding portion 106b and a second protruding portion 106c. The first strut 104a may comprise a first strut connector 108a and a second strut connector 108c. The second strut 104b may comprise a first strut connector 108b and a second strut connector 108d. The first strut 104a may comprise a first rotational joint member 136a and a second rotational joint member 136c. The second strut 104b may comprise a first rotational joint member 136b and a second rotational joint member 136d.

As shown in FIG. 2A, the first rotational joint member 136a and the second rotational joint member 136c of the first strut 104a may be positioned such that the first strut is substantially straight. Likewise, the first rotational joint member 136b and the second rotational joint member 136d of the second strut 104b may be positioned such that the second strut is substantially straight. Alternatively, as shown in FIG. 2B, the first rotational joint member 136a and the second rotational joint member 136c of the first strut 104a may be positioned such that the first strut is bent. Likewise, the first rotational joint member 136b and the second rotational joint member 136d of the second strut 104b may be positioned such that the second strut is bent.

As shown in FIG. 1, the strut connectors 108a, 108b, 108c, and 108d may be positioned with the first strut 104a and the second strut 104b releasably positioned substantially parallel to the upper surfaces 110 and the lower surfaces 112 of the first frame member 102a and the second frame member 102b, thus placing the collapsible fixator system 100 in the first, collapsed position. Alternatively, as shown in FIG. 2A, the strut connectors 108a, 108b, 108c, and 108d may be positioned with the first strut 104a and the second strut 104b fixedly positioned substantially perpendicular in relation to the upper surfaces 110 and the lower surfaces 112 of the first frame member 102a and the second frame member 102b, thus placing the collapsible fixator system 100 in the second, erect position such that the first frame member 102a and the second frame member 102b are fixedly spaced apart from one another. In other embodiments, the collapsible fixator system 100 may be placed in the second, erect position such that the first frame member 102a and the second frame member 102b are fixedly spaced apart from one another, without the first strut 104a and the second strut 104b positioned substantially perpendicular in relation to the upper surfaces 110 and the lower surfaces 112 of the first frame member 102a and the second frame member 102b. As shown in FIG. 2B, the rotational joint members 136a, 136b, 136c, and 136d are positioned such that the first strut 104a and the second strut 104b are bent; thus, the strut connectors 108a, 108b, 108c, and 108d may be positioned to place the collapsible fixator system 100 in the second, erect position such that the first frame member 102a and the second frame member 102b are fixedly spaced apart from one another without the first strut 104a and the second strut 104b being positioned substantially perpendicular in relation to the upper surfaces 110 and the lower surfaces 112 of the first frame member 102a and the second frame member 102b.

Figure 3:
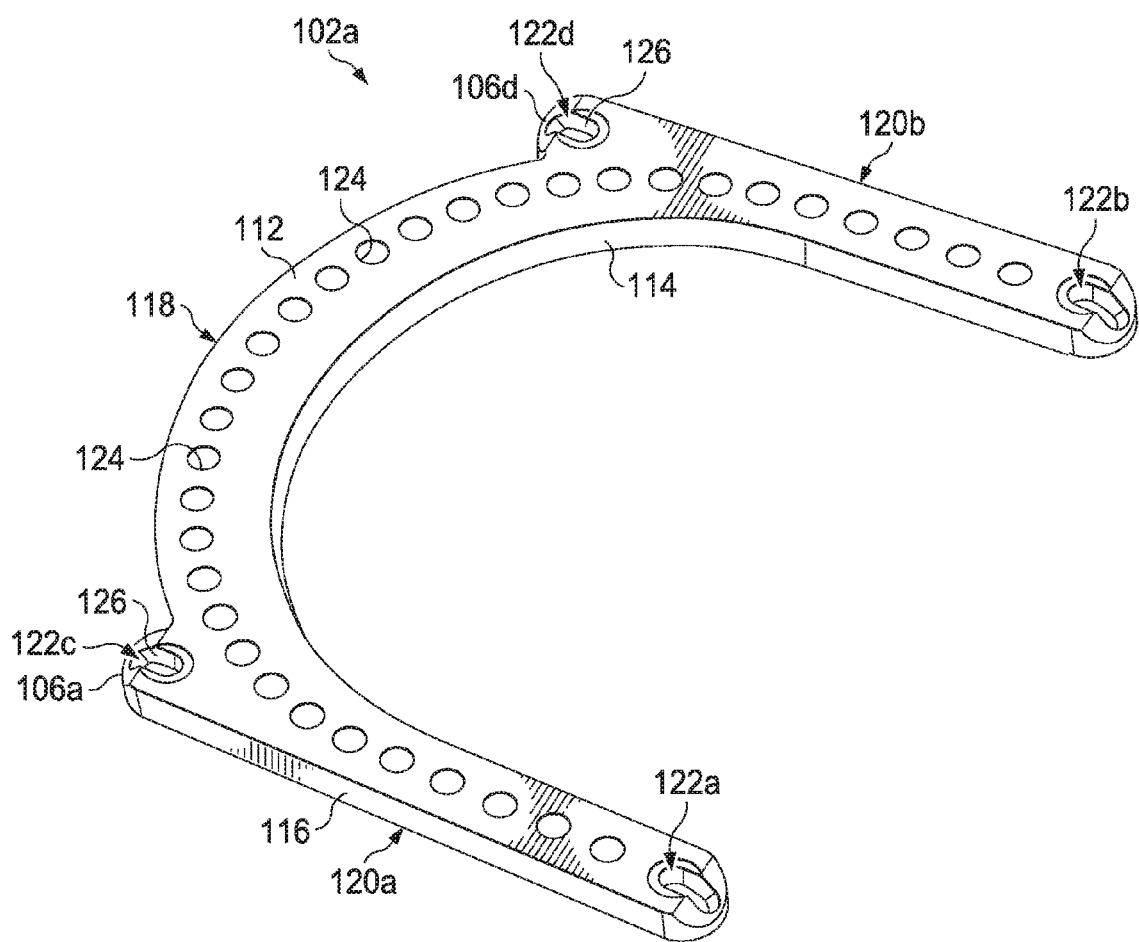
FIG. 3 illustrates an isometric view of a frame member depicted in FIGS. 1, 2A, and 2B, in accordance with one embodiment of the present disclosure.

FIG. 3 illustrates an isometric view of the frame member 102 depicted in FIGS. 1 and 2, in accordance with one embodiment of the present disclosure. As shown in FIG. 3, the frame member 102 may further comprise a first arm 120a, a second arm 120b, and a connecting portion 118 defined there between. The first arm 120a may comprise a first aperture 122a and the second arm 120b may comprise a second aperture 122b. The first protruding portion 106a may comprise a third aperture 122c and the second protruding portion 106d may comprise a fourth aperture 122d. In some embodiments, as shown in FIG. 3, the first protruding portion 106a of the frame member 102 may be proximate to the first arm 120a and the connecting portion 118. The second protruding portion 106d may be proximate to the second arm 120b and the connecting portion 118.

The first aperture 122a, the second aperture 122b, the third aperture 122c, and the fourth aperture 122d may extend through the upper surface 110 of the frame member 102 to the lower surface 112 (as shown in FIG. 1) of the frame member 102 thereby forming an aperture hole 126. In some embodiments, at least one of the first aperture 122a, second aperture 122b, third aperture 122c, and fourth aperture 122d comprises an upper portion and a lower portion operable to interact with a strut connector.

As shown in FIG. 3, the frame member 102 may comprise a plurality of top holes 124 such that each of the plurality of top holes 124 extends through the upper surface 110 (as shown in FIG. 1) of the frame member 102 to the lower surface 112 of the frame member 102. In some embodiments, a uniform amount of space may be present between each of the plurality of top holes 124, such as every 0.5 cm, every 1 cm, etc. In other embodiments the amount of space present between each of the plurality of top holes 124 may be irregular or varying. The plurality of top holes 124 may receive one or more fixation bolts (not shown). The one or more fixation bolts may be used to secure a plurality of pins and wires (not shown) to the frame member 102. The plurality of pins and wires (not shown) may be attached to one or more bone fragments. The one or more fixation bolts (not shown) may be used to secure one or more hardware components (e.g. plates, posts, threaded or telescopic rods) to the frame member 102.

The frame member 102 may further comprise a plurality of side holes (not shown) such that each of the plurality of side holes (not shown) extends through the inner surface 114 of the frame member 102 to the outer surface 116 of the frame member 102. In some embodiments, a uniform amount of space may be present between each of the plurality of side holes (not shown) such as every 0.5 cm, every 1 cm, etc. In other embodiments the amount of space present between each of the plurality of side holes (not shown) may be irregular or varying. The plurality of side holes may receive one or more connection elements (e.g. struts or other mechanical links used to connect a first fixator frame to a second fixator frame) such that the collapsible fixator system 100 is semi-permanently or permanently attached to an affected patient. Alternatively, the plurality of side holes may receive and secure hardware components (e.g. plates, posts, threaded or telescopic rods).

Figure 4:
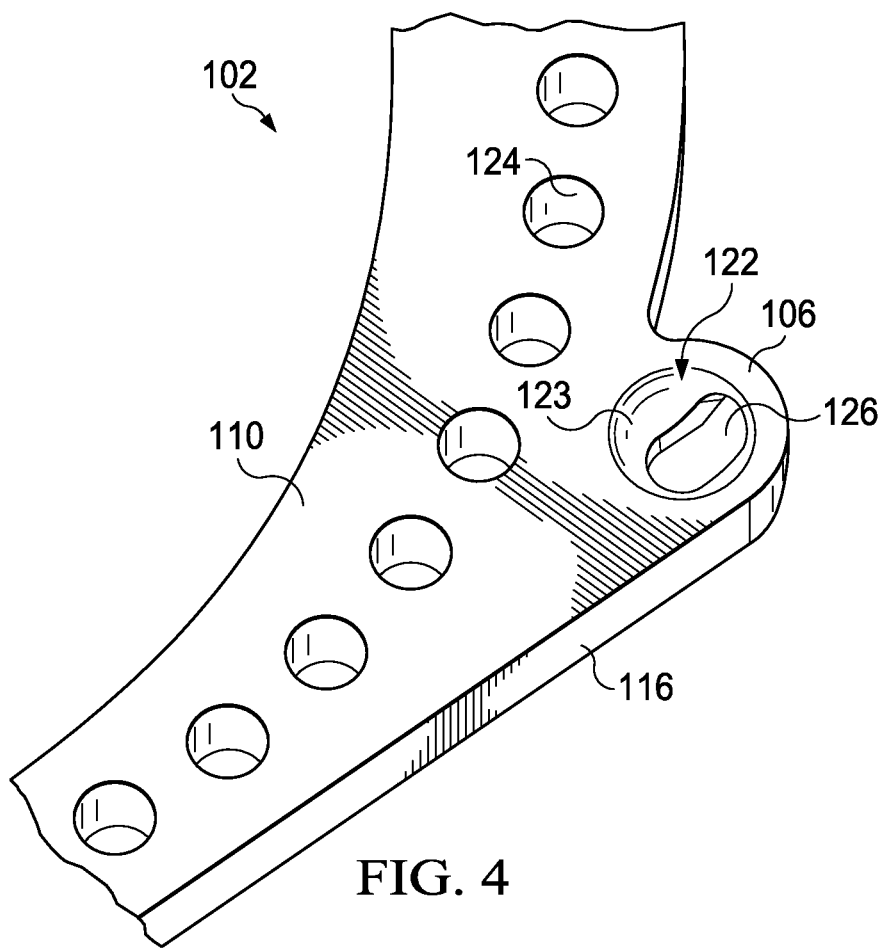
FIG. 4 illustrates a close-up view of an upper surface and protruding portion of the frame member depicted in FIG. 3, in accordance with one embodiment of the present disclosure.
Figure 5:
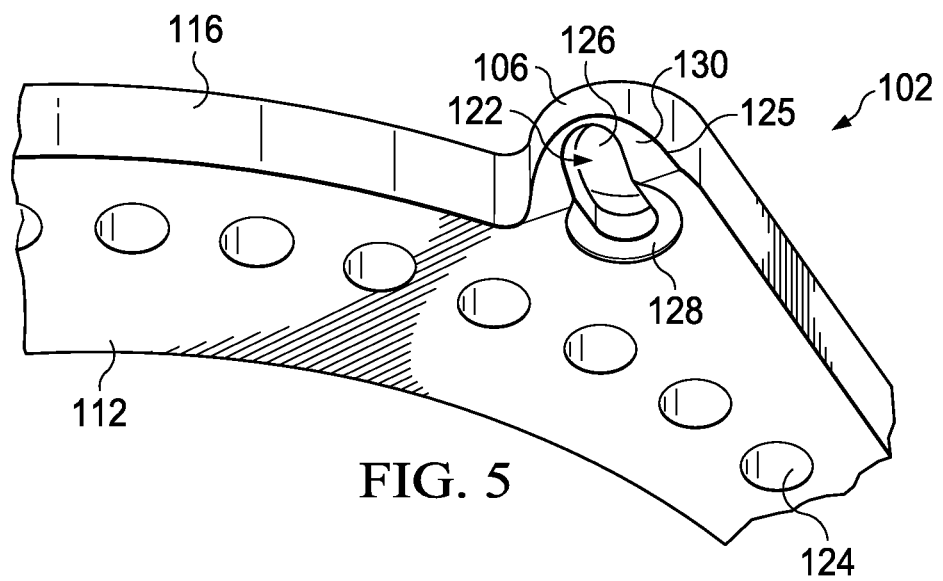
FIG. 5 illustrates a close-up view of a lower surface and protruding portion of the frame member depicted in FIG. 4, in accordance with one embodiment of the disclosure.
Figure 11:
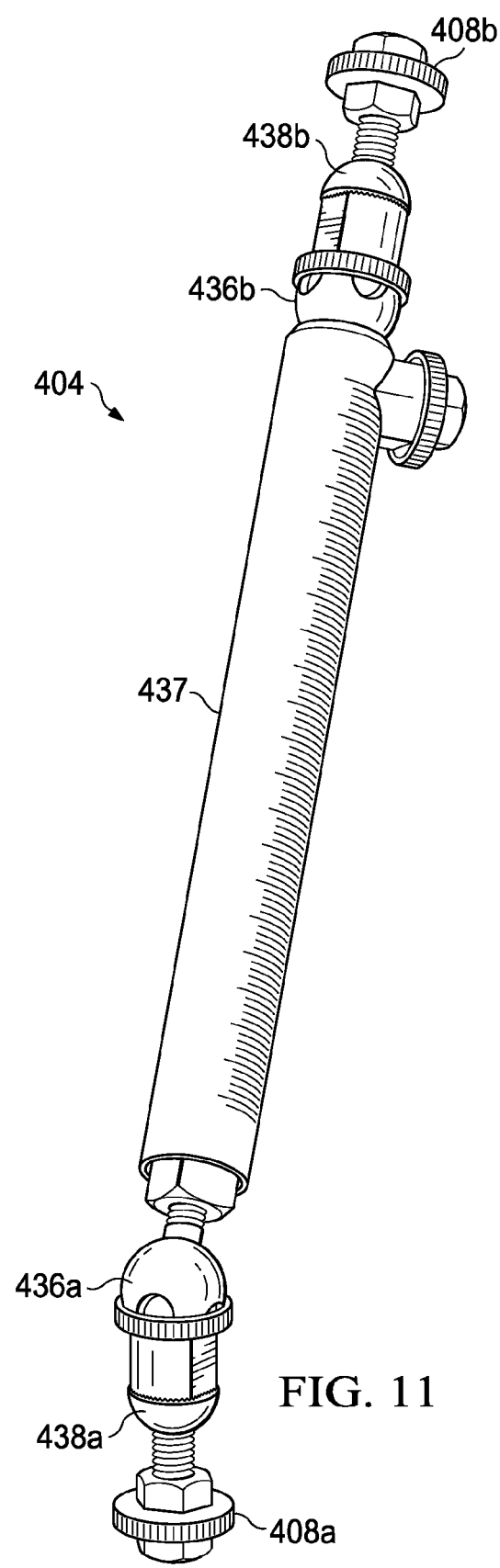
FIG. 11 illustrates an isometric view of a strut, in accordance with one embodiment of the disclosure.

FIG. 4 illustrates an close-up view of the upper surface 110 at a protruding portion 106 of the frame member 102 depicted in FIG. 3, in accordance with one embodiment of the present disclosure. As shown in FIG. 4, the aperture 122 may extend through the upper surface 110 of the frame member 102 to the lower surface 112 (as shown in FIG. 1) of the frame member 102 thereby forming the aperture hole 126. The aperture 122 may further comprise an upper portion 123 and a lower portion (e.g. 125 as shown in FIG. 5). As shown in FIG. 4, the upper portion 123 may comprise a recessed area defined within the upper surface 110 of the frame member 102. The upper portion 123 may be operable to receive a hemispherical feature (e.g. 438a as shown in FIG. 11) of a strut (e.g. 104a as shown in FIG. 1).

FIG. 5 illustrates a close-up view of a lower surface 112 at a protruding portion 106 of the frame member 102 depicted in FIG. 4, in accordance with one embodiment of the disclosure. As shown in FIG. 5, the frame member 102 may comprise the upper surface (not shown), the lower surface 112, the inner surface (not shown), the outer surface 116, the aperture 122, the aperture hole 126, a leveled portion 128, and an inclined portion 130.

The aperture 122 comprises the upper portion (123, as shown in FIG. 4) and the lower portion 125. In some embodiments, as shown in FIG. 5, the lower portion 125 may comprise the leveled region 128 and the inclined region 130. The leveled region 128 may be substantially parallel to and defined within the lower surface 112 of the frame member 102 and operable to interact with the first or the second strut connector (e.g. 108a, 108c, as shown in FIG. 1) when the collapsible fixator system is in the second, erect position. The leveled region 128 may further comprise an indentation of the lower surface 112 of frame member 102, with the leveled region 128 surrounding at least a portion of the aperture hole 126. In other embodiments the leveled region 128 may be raised above the lower surface 112 or may be level with the lower surface 112 of the frame member 102. The inclined region 130 may gradually slope from the lower surface 112 at the outer surface 116 to the leveled region 128, and may be operable to interact with the first or the second strut connector (e.g. 108a, 108c, as shown in FIG. 2) when the collapsible fixator system is in the first, collapsed position. In some embodiments, and as shown in FIG. 5, the inclined region 130 may consist of at least a portion of the lower surface 112 of the protruding portion 106 of the frame member 102. In other embodiments, the inclined region 130 may extend beyond the protruding portion 106 and may include other portions of the lower surface 112 of the frame member 102. In one embodiment, the inclined region 130 may be sloped at an angle of approximately 45 degrees. The first or the second strut connector (e.g. 108a, 108c, as shown in FIG. 1) may be releasably attached to the inclined region 130 such that the strut may be positioned substantially parallel to the upper surfaces and the lower surfaces 112 of the first frame member 102a and the second frame member 102b, thus placing the collapsible fixator system 100 in the first, collapsed position. In other embodiments, the inclined region 130 may be sloped at an angle less than 45 degrees.

In operation, the aperture 122 may be configured to receive a strut (e.g. 104a as shown in FIGS. 1 and 2) through the aperture hole 126 such that a first end of the strut extends through the lower surface of the first fixator member 102a to the upper surface 110 of the first fixator member 102a (as shown in FIG. 1), and the strut may be releasably and adjustably attached to the first fixator member 102a by a strut connector (e.g. 108a as shown in FIGS. 1 and 2) secured to the first end of the strut.

Figure 6:
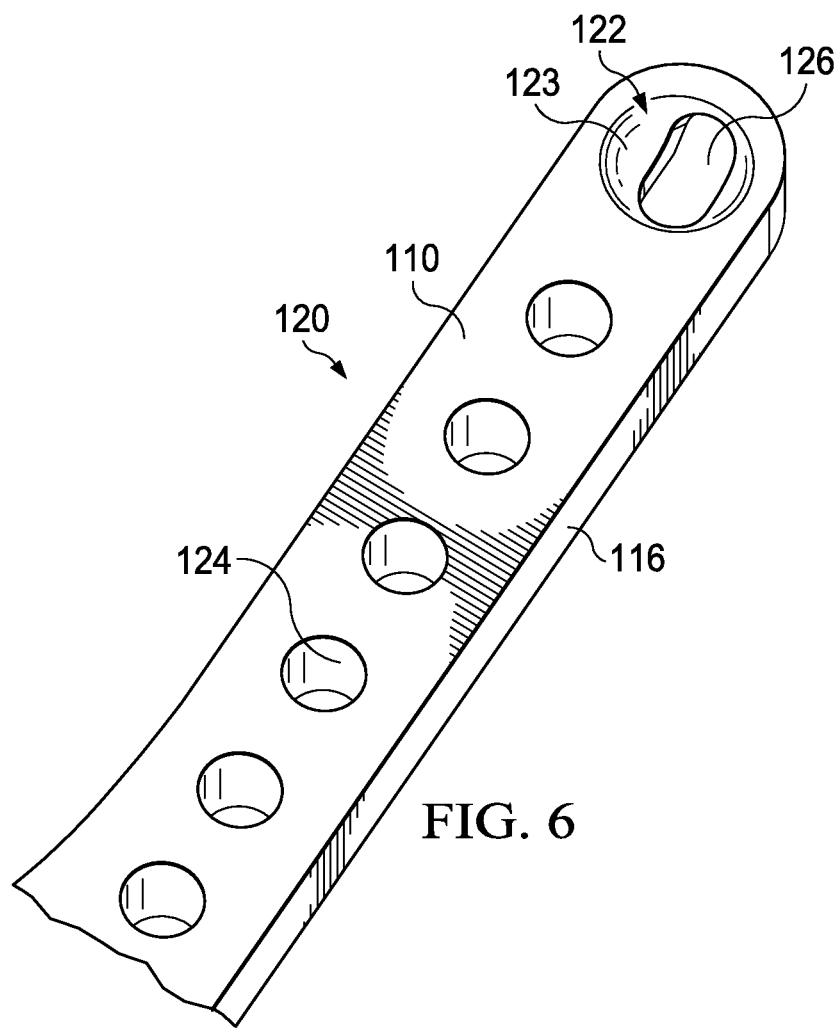
FIG. 6 illustrates a close-up view of the upper surface and arm portion of the frame member depicted in FIG. 3, in accordance with one embodiment of the disclosure.
Figure 7:
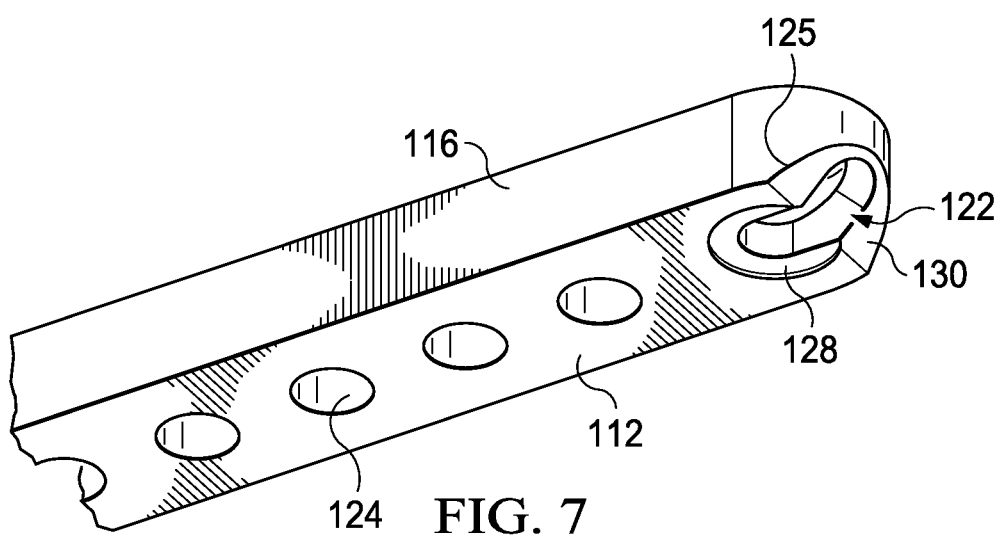
FIG. 7 illustrates a close-up view of the lower surface and arm portion of the frame member depicted in FIG. 3, in accordance with one embodiment of the disclosure.

FIG. 6 illustrates a close-up view of the upper surface 110 at an arm portion 120 of the frame member 102 depicted in FIG. 3, in accordance with one embodiment of the disclosure. As shown in FIG. 6, the frame member 102 may comprise the upper surface 110, the lower surface (not shown), the inner surface (not shown), the outer surface 116, the aperture 122, and the aperture hole 126. The aperture 122 may extend through the upper surface 110 of the frame member 102 to the lower surface 112 (as shown in FIG. 1) of the frame member 102 thereby forming the aperture hole 126. In some embodiments, the aperture 122 comprises the upper portion 123 and the lower portion (e.g. 125 as shown in FIG. 7). As shown in FIG. 6, the upper portion 123 may comprise a recessed area defined within the upper surface 110 of the frame member 102. The upper portion 123 may be operable to receive a hemispherical feature (e.g. 438a as shown in FIG. 11) of a strut (e.g. 104a as shown in FIG. 1).

FIG. 7 illustrates a close-up view of the lower surface 112 of the frame member 102 depicted in FIG. 3 at the location of the arm portion 120, in accordance with one embodiment of the disclosure. As shown in FIG. 7, the frame member 102 may comprise the upper surface (not shown), the lower surface 112, the inner surface (not shown), the outer surface 116, the aperture 122, the leveled aperture portion 128, and the inclined aperture portion 130.

The aperture 122 comprises the upper portion 123, as shown in FIG. 6) and the lower portion 125. In some embodiments, as shown in FIG. 7, the lower portion 125 may comprise the leveled region 128 and the inclined region 130. The leveled region 128 may be substantially parallel to and defined within the lower surface 112 of the frame member 102 and operable to interact with the first or the second strut connector (e.g. 108a, 108c, as shown in FIG. 2) when the collapsible fixator system is in the second, erect position. The leveled region 128 may further comprise an indentation of the lower surface 112 of frame member 102, with the leveled region 128 surrounding at least a portion of the aperture hole 126. In other embodiments the leveled region 128 may be raised above the lower surface 112 or may be level with the lower surface 112 of the frame member 102. The inclined region 130 may gradually slope from the lower surface 112 at the outer surface 116 to the leveled region 128, and may be operable to interact with the first or the second strut connector (e.g. 108a, 108c, as shown in FIG. 1) when the collapsible fixator system is in the first, collapsed position. In an embodiment, the inclined region 130 may be sloped at an angle of approximately 45 degrees. The first or the second strut connector (e.g. 108a, 108c, as shown in FIG. 1) may be releasably attached to the inclined region 130 such that the strut may be positioned substantially parallel to the upper surfaces and the lower surfaces 112 of the first frame member 102a and the second frame member 102b, thus placing the collapsible fixator system 100 in the first, collapsed position. In other embodiments, the inclined region 130 may be sloped at an angle less than 45 degrees.

In operation, the aperture 122 may be configured to receive a strut (e.g. 104a as shown in FIGS. 1 and 2) through the aperture hole 126 such that a first end of the strut extends through the upper surface 110 of the second fixator member 102b to the lower surface 112 of the second fixator member 102a (as shown in FIG. 1), and the strut may be adjustably attached to the fixator member 102 by a strut connector (e.g. 108a as shown in FIGS. 1 and 2) secured to the second end of the strut.

Figure 8:
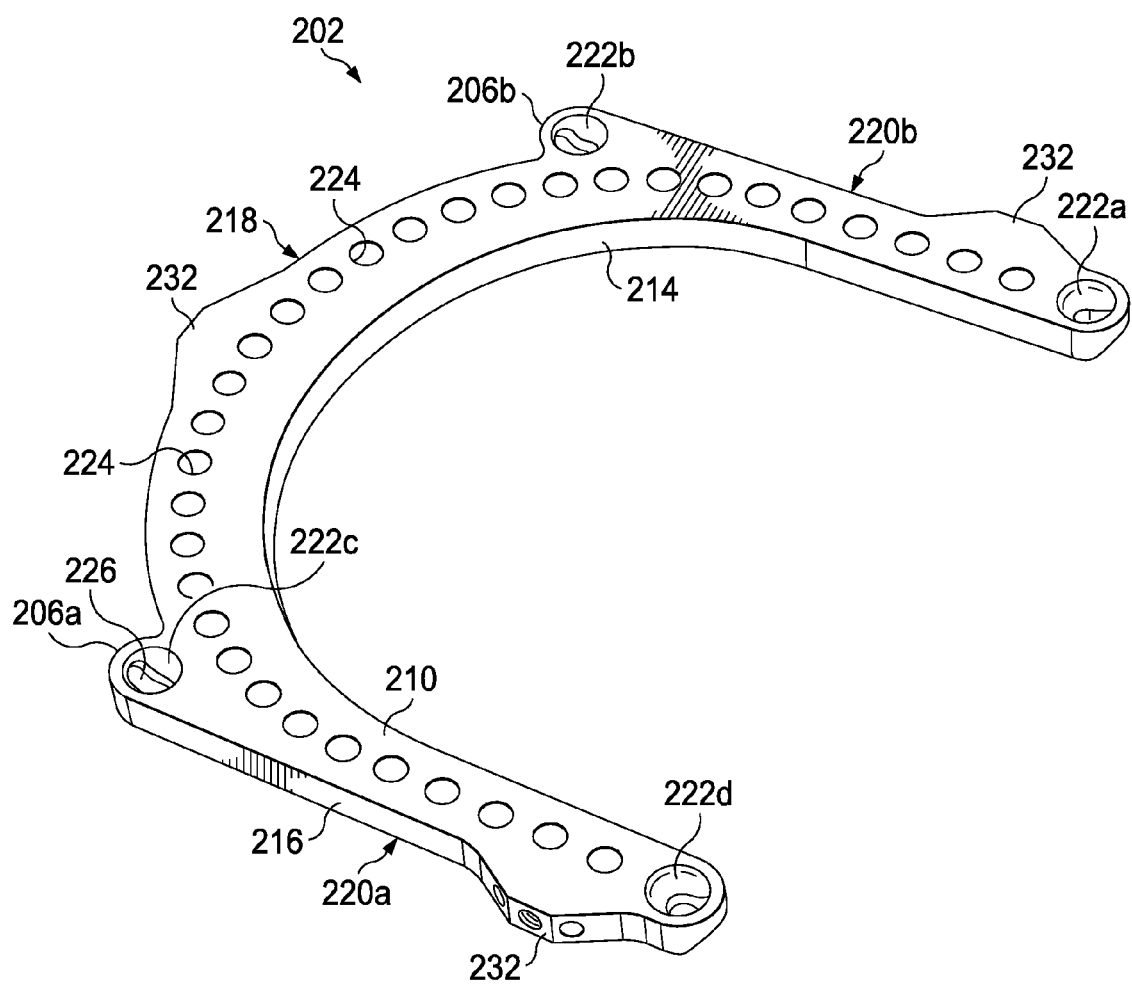
FIG. 8 illustrates an isometric view of a frame member, in accordance with one embodiment of the disclosure.

FIG. 8 illustrates an isometric view of a frame member 202, in accordance with one embodiment of the present disclosure. As shown in FIG. 8, the frame member 202 may comprise a first arm 220a, a second arm 220b, a connecting portion 218 defined there between, an upper surface 210, a lower surface (not shown), an inner surface 214, an outer surface 216, a first protruding portion 206a, a second protruding portion 206b, a first aperture 222a, a second aperture 222b, a third aperture 222c, a fourth aperture 222d, a plurality of top holes 224, and at least one flange 232. In one embodiment, the frame member 202 may have a substantially U-shape, as shown in FIG. 8, comprising a first arm 220a, a second arm 220b, and a connecting portion 218. In other embodiments, the frame member 202 may be a substantially ring shape, an oval shape, a partial ring shape, or a plate shape. As shown in FIG. 8, the second arm member 220b may comprise the first aperture 222a, the second protruding portion 206b may comprise the second aperture 222b, the first protruding portion 206a may comprise the third aperture 222c, and the first arm member 220a may comprise the fourth aperture 222d. The first aperture 222a, second aperture 222b, third aperture 222c, and fourth aperture 222d may extend through the upper surface 210 of the frame member 202 to the lower surface (not shown) of the frame member 202 thereby forming an aperture hole 226. In some embodiments, at least one of the first aperture 222a, second aperture 222b, third aperture 222c, and fourth aperture 222d may be configured to receive a strut (e.g. 104a as shown in FIGS. 1 and 2) through the aperture hole 226 such that a first end of the strut extends through the upper surface 210 of the frame member 202 to the lower surface (not shown) of the frame member 202, and the strut may be removably and adjustably attached to the frame member 202 by a strut connector (e.g. 108a as shown in FIGS. 1 and 2) secured to the first end of the strut on the lower surface (not shown) of the frame member 202.

As shown in FIG. 8, the frame member 202 may comprise a plurality of top holes 224 such that each of the plurality of top holes 224 extends through the upper surface 210 of the fixator member 202 to the lower surface (not shown) of the fixator member 202. In some embodiments, a uniform amount of space may be present between each of the plurality of top holes 224 such as every 0.5 cm, every 1 cm, etc. In other embodiments the amount of space present between each of the plurality of top holes 224 may be irregular or varying. The plurality of top holes 224 may receive one or more fixation bolts (not shown). The one or more fixation bolts may be used to secure a plurality of pins and wires (not shown) to the frame member 202. The plurality of pins and wires (not shown) may be attached to one or more bone fragments. The one or more fixation bolts (not shown) may be used to secure one or more hardware components (e.g. plates, posts, threaded or telescopic rods) to the frame member 202.

The frame member 202 may comprise a plurality of side holes (not shown) such that each of the plurality of side holes (not shown) extends through the inner surface 214 of the fixator member 202 to the outer surface 216 of the frame member 202. In some embodiments, a uniform amount of space may be present between each of the plurality of side holes (not shown) such as every 0.5 cm, every 1 cm, etc. In other embodiments the amount of space present between each of the plurality of side holes (not shown) may be irregular or varying. The plurality of side holes may receive one or more connection elements (e.g. struts or other mechanical links used to connect a first fixator frame to a second fixator frame) such that the collapsible fixator system 100 is semi-permanently or permanently attached to an affected patient. Alternatively, the plurality of side holes may receive and secure hardware components (e.g. plates, posts, threaded or telescopic rods).

The present invention can use multiple struts and it may be desirable to be able to uniquely identify each strut so that the strut length adjustments for each strut can be tracked and implemented. An information indicator may be mounted onto or embedded into the struts for identifying the struts. In some embodiments, the information indicator may be a physical identifier, such as inscription, paper, or label of a code, color, or serial number corresponding to relevant information. Examples of the relevant information embodied or represented by the information indicator may include the type of the strut, the maximum or minimum strut length, strut number, etc. In some embodiments, the information indicator may be an electronic identifier. One common method of identification includes a radio frequency (RF) sensor that wirelessly communicates with a radio frequency transmitter (RFID) located on the adjustment mechanism of the strut. Another strut number identifier may include a bar code reader that counts a specific number of grooves on the adjustment mechanism of the strut or communicates with magnetic strip located on the adjustment mechanism of the strut. In another embodiment, strut number identifier includes a sensor that receives information from a touch memory button located on the adjustment mechanism of the strut. In other embodiments, the information indicator may be any other device suitable to embody or represent information or a combination of the types of indicators discussed in the present application.

As shown in FIG. 8, the frame member 202 may comprise the at least one flange 232. In one embodiment, as shown in FIG. 8, the at least one flange 232 may be trapezoidal and proximate to and extending from the first arm 220a, the second arm 220b, the connecting portion 218, or combinations thereof. The at least one flange 232 may be connected at any point along the first arm 220a, the second arm 220b, or the connecting portion 218. In other embodiments wherein the frame member 202 does not constitute a substantially U-shape, the at least one flange 232 may be connected to the frame member 202 at any point along the outer surface 216.

Figure 9:
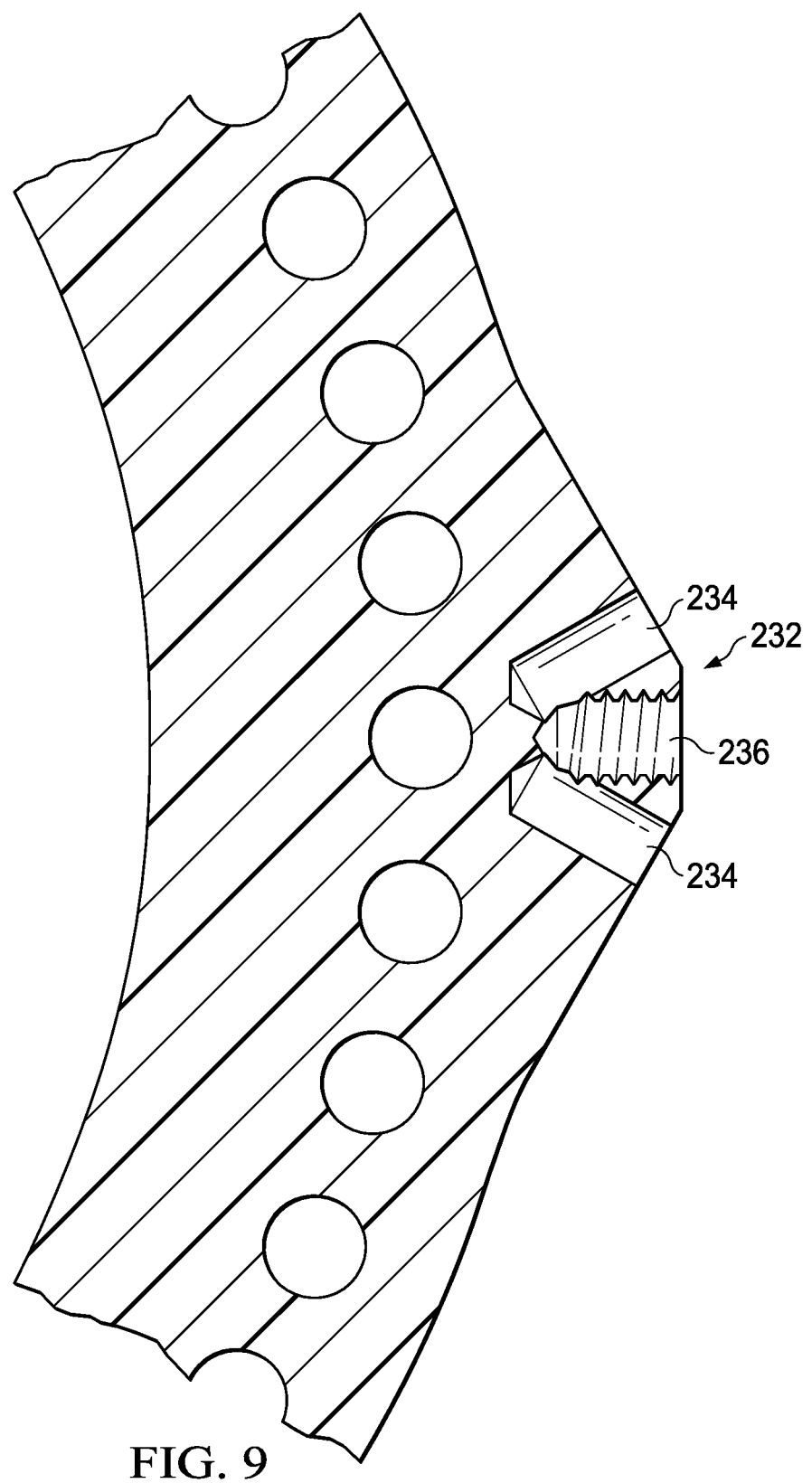
FIG. 9 illustrates a cutaway view of a flange located on the frame member, in accordance with one embodiment of the disclosure.

FIG. 9 illustrates a partial cut-away of the at least one flange 232 located on the frame member 202, in accordance with one embodiment of the disclosure. The at least one flange 232 may comprise at least one mounting surface for connecting connection struts (not shown). Each mounting surface includes an aperture 234 defined therein. The apertures 234 each have a smooth (rather than threaded) inner surface and are adapted to receive studs from the connection struts. The at least one flange 232 may further comprise a securing surface disposed between the mounting surfaces. The securing surface has an aperture 236 defined therein, and the aperture 236 is operable to receive a screw for locking the studs in place. In an embodiment, the screw may be a set screw.

Figure 10:
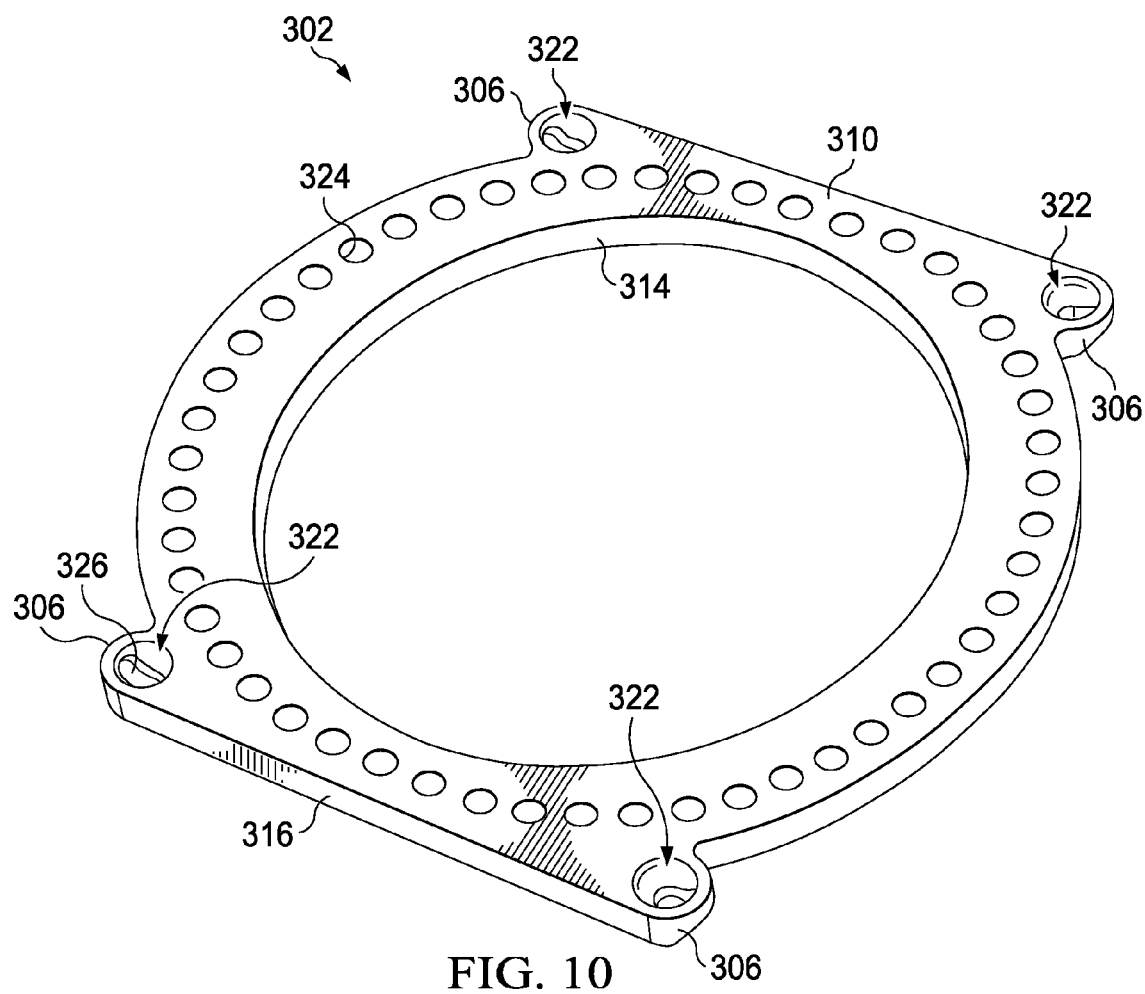
FIG. 10 illustrates an isometric view of a circular frame member, in accordance with one embodiment of the disclosure.

FIG. 10 illustrates an isometric view of a frame member 302, in accordance with one embodiment of the present disclosure. As shown in FIG. 10, the frame member 302 may be circular and may comprise an upper surface 310, a lower surface (not shown), an inner surface 314, an outer surface 316, a plurality of protruding portions 306, a plurality of apertures 322, and a plurality of top holes 324. Like the frame members described above, the frame member 302 may comprise a plurality of apertures 322. In other embodiments, the frame member 302 may comprise at least a first aperture. Each of the plurality of apertures 322 may extend through the upper surface 310 of the fixator member 302 to the lower surface (not shown) of the fixator member 302 thereby forming an aperture hole 326. In some embodiments, at least one of the plurality of apertures 322 comprises an upper portion and a lower portion. The upper portion may comprise a recessed area defined within the upper surface 310 of the frame member 302. The upper portion may be operable to receive a hemispherical feature (e.g. 438a as shown in FIG. 11) of a strut (e.g. 104a as shown in FIG. 1). In some embodiments at least one of the plurality of apertures 322 may be configured to receive a strut (e.g. 104a as shown in FIGS. 1 and 2) through the aperture hole 326.

FIG. 11 illustrates an elevational view of a strut 404, in accordance with one embodiment of the disclosure. The strut 404 may comprise a first strut connector 408a, a second strut connector 408b, a first rotational joint member 436a, a second rotational joint member 436b, a body 437, a first hemispherical feature 438a, and a second hemispherical feature 438b. The first strut connector 408a may be disposed on a first end of the strut 404. The second strut connector 408b may be disposed on a second end of the strut 404. The body 437 may be positioned between first strut connector 408a and the second strut connector 408b. The first rotational joint member 436a may be positioned between the body 437 and the first strut connector 408a. The second rotational joint member 436b may be positioned between the body 437 and the second strut connector 408b. The first hemispherical feature 438a may be positioned between the first rotational joint member 436a and the first strut connector 408a. The second hemispherical feature 438b may be positioned between the second rotational joint member 436b and the second strut connector 408b.

The strut 404 may comprise at least one threaded end such that the strut connector 408 may releasably attach to the threaded end. The strut connector 408 may be configured to releasably (e.g. tighten, un-tighten) or fixedly attach the strut 404 to a frame member. In some embodiments the strut connector may be internally threaded (e.g. nut, hex nut, wing nut) to releasably connect to a threaded end of the strut 404. In other embodiments, the strut connector 408 may fixedly connect (e.g. tubular rivet) to an end of the strut 404. Connection of the strut connector 408 to the strut 404 may be manually performed in some embodiments, but in other embodiments may require specialized tools.

The first and second strut connectors 408a, 408b may further be operable to rotate relative to the first and second hemispherical features 438a, 438b, respectively, thereby lengthening or shortening the first and second strut connectors 408a, 408b relative to the first and second hemispherical features 438a, 438b.

At least one of the first hemispheric feature 438a or the second hemispheric feature 438b may be operable to rotate within an upper portion (e.g. 123, as shown in FIG. 6) of an aperture (e.g. 122, as shown in FIG. 6) such that the corresponding strut connector (e.g. 408a) is operable to reversibly transitions between the first, collapsed position (as shown in FIG. 1) and the second, erect position (as shown in FIGS. 2A and B).

The first rotational joint member 436a may be operable to rotate the first strut connector 408a and the body 437 relative to one another. The second rotational joint member 436b may be operable to rotate the second strut connector 408b and the body 437 relative to one another. In some embodiments, and as shown in FIG. 11, at least one of the first rotational joint member 436a and the second rotational joint member 436b may be a passive ball-and-socket joint. However, in other embodiments, the rotational joint member may be a universal joint, a heim joint, a johnny joint, or any joint known by one skilled in the art that would allow the range of motion described herein.

Figure 13:
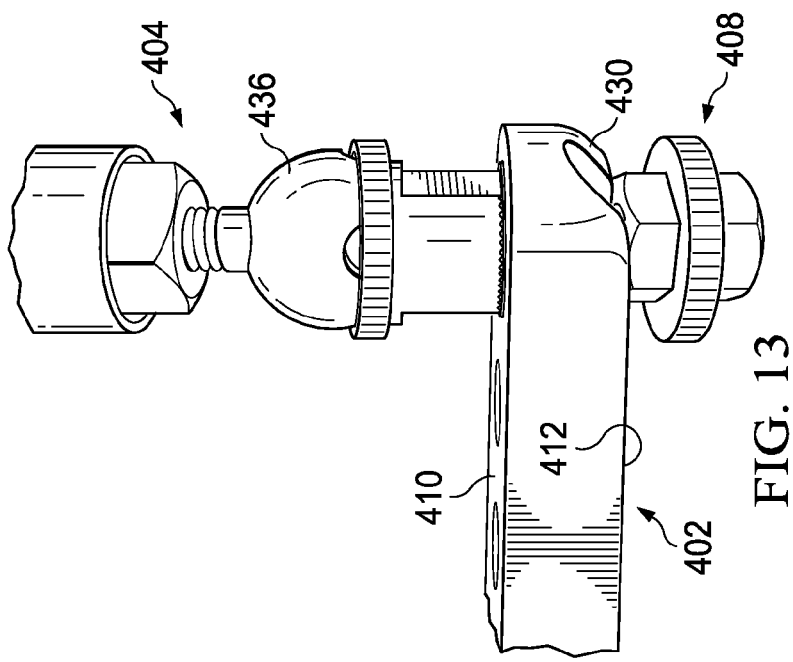
FIG. 13 illustrates a close-up view of the strut connected to the frame member depicted in FIG. 12 in a second, erect position, in accordance with one embodiment of the disclosure.
Figure 12:
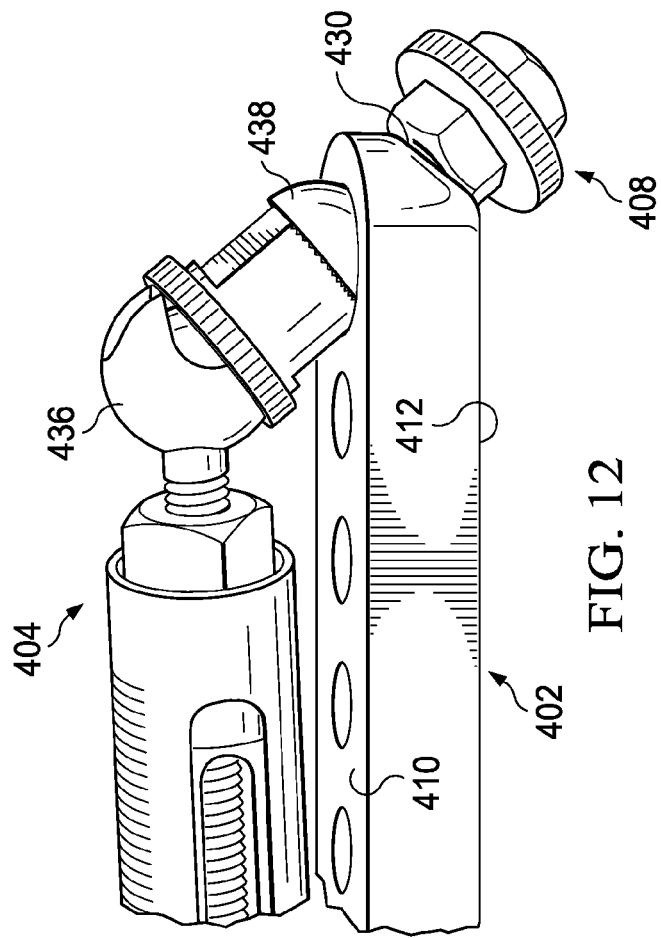
FIG. 12 illustrates a close-up view of a strut connected to a frame member in a first, collapsed position, in accordance with one embodiment of the disclosure.

FIG. 12 illustrates close-up view of a strut 404 connected to a frame member 402 in the first, collapsed position, in accordance with one embodiment of the disclosure. FIG. 13 illustrates a close-up view of the strut 404 connected to the frame member 402 depicted in FIG. 12 in the second, erect position, in accordance with one embodiment of the disclosure. The strut 404 may comprise the strut connector 408, the rotational joint member 436, and the hemispheric feature 438. The frame member 402 may comprise an upper surface 410, a lower surface 412, an aperture (not shown), a leveled aperture portion (not shown), and an inclined aperture portion 430. As shown in FIG. 12, the strut connector 408 may be configured in a first position with the strut 404 releasably positioned substantially parallel in relation to the upper surface 410 and the lower surface 412 of the frame member 402, thus rendering the collapsible fixator system in a collapsed position. As shown in FIG. 13, the strut connector 408 may be configured in a second position with the strut 404 positioned substantially perpendicular in relation to the upper surface 410 and the lower surface 412 of the frame member 402, thus rendering the collapsible fixator system 100 in the second, erect position such that the first frame member 102a and the second frame member 102b are fixedly spaced apart from one another. In other embodiments, the collapsible fixator system 100 may be placed in the second, erect position such that the first frame member 102a and the second frame member 102b are fixedly spaced apart from one another, without the first strut 104a and the second strut 104b positioned substantially perpendicular in relation to the upper surfaces 110 and the lower surfaces 112 of the first frame member 102a and the second frame member 102b (as shown in FIG. 2B).

In operation, and in order to transition between the first, collapsed position and the second, erect position, a surgeon may loosen the strut connector 408, thereby lengthening the strut connector 408 away from the lower surface 412 of the frame 402. When the strut connector 408 is lengthened away from the frame 402, the hemispheric feature 438 is operable to rotate within the aperture (not shown) and the strut connector is operable to be positioned proximate to either the lower surface 412 or the inclined portion 430 of the frame member 402. In the first, collapsed position, the strut connector 408 may be tightened against the inclined portion 430 of the frame member 402. In the second, erect position, the strut connector 408 may be tightened against the lower surface 412 of the frame member 402. One or more components of the collapsible fixator frame and strut system disclosed herein may be made from any of the following materials: (a) any biocompatible material (which biocompatible material may be treated to permit bone ingrowth or prohibit bone ingrowth); (b) a plastic; (c) a wood; (d) a fiber; (e) a polymer (e.g. polypropylene, polystyrene, polyurethane, latex, nylon; (f) a metal (e.g., a pure metal such as titanium, chromium, or copper and/or an alloy such as Ti-Al-Nb, TI-6Al-4V, stainless steel, bronze); (g) a radioluscent material (e.g., carbon fiber PEEK or aluminum); (h) a ceramic; (i) a rubber) or (j) any combination thereof. Furthermore, one or more components of the collapsible fixator frame and strut system may be varied in size for use by both pediatric and adult patients.

The methods of the present disclosure may be performed with a subject (e.g., a human or another vertebrate animal). One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

The collapsible fixation system 100 may be connected to the selected bone(s). Connection may be performed at any suitable time, such as before, during, and/or after construction of the collapsible fixation device. For example, the collapsible fixation device may be assembled and then connected to bone, or individual collapsible fixation device members or collapsible fixation device sub-assemblies may be connected to the bone before the collapsible fixation device is fully assembled. Connection of the collapsible fixation device to bone may include placing connectors, such as wires, pins, screws, and/or rods, among others through the skin and into, through, and/or around the selected bone.

Figure 14A:
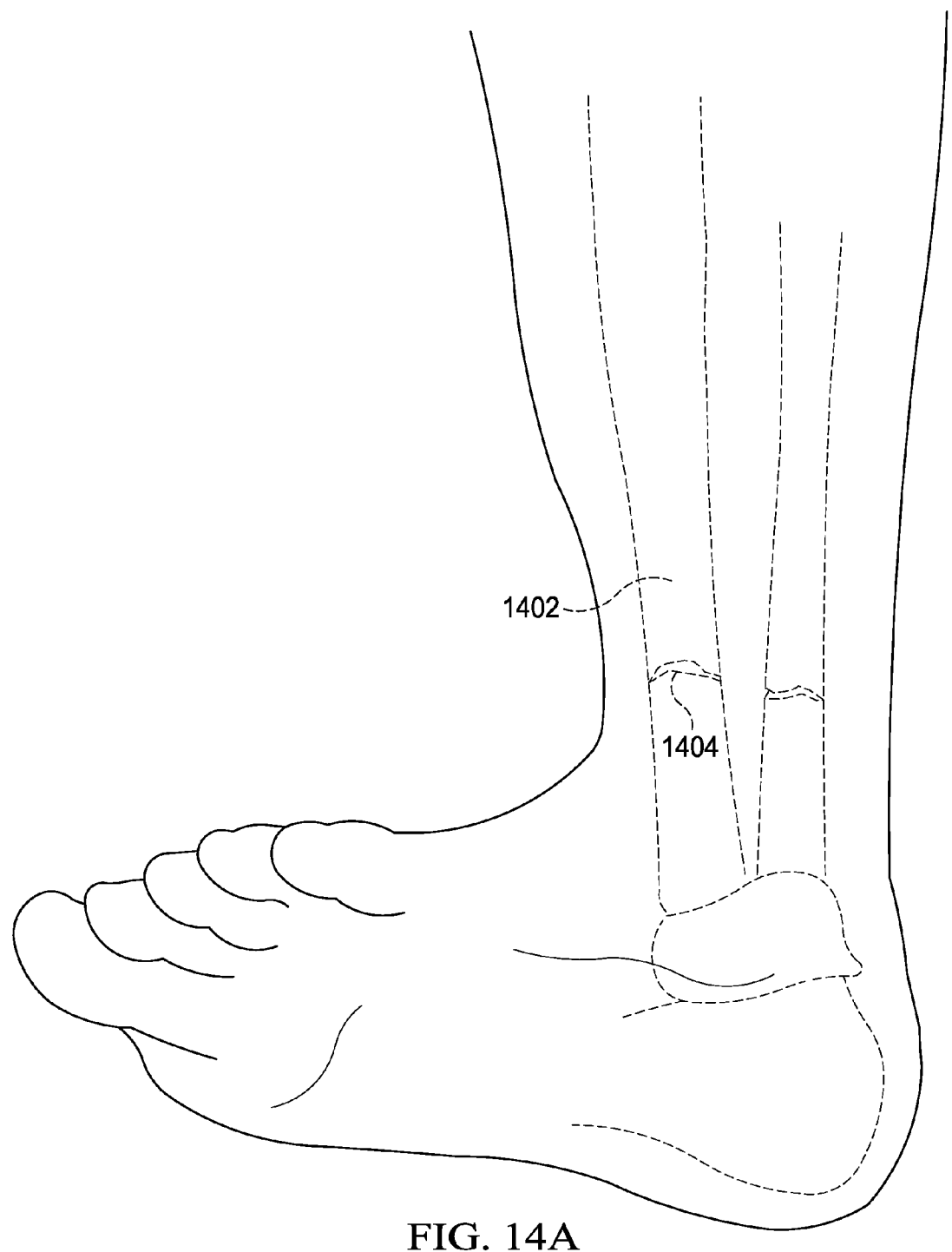
FIG. 14A illustrates a frontal view of a fractured human tibia bone.
Figure 14B:
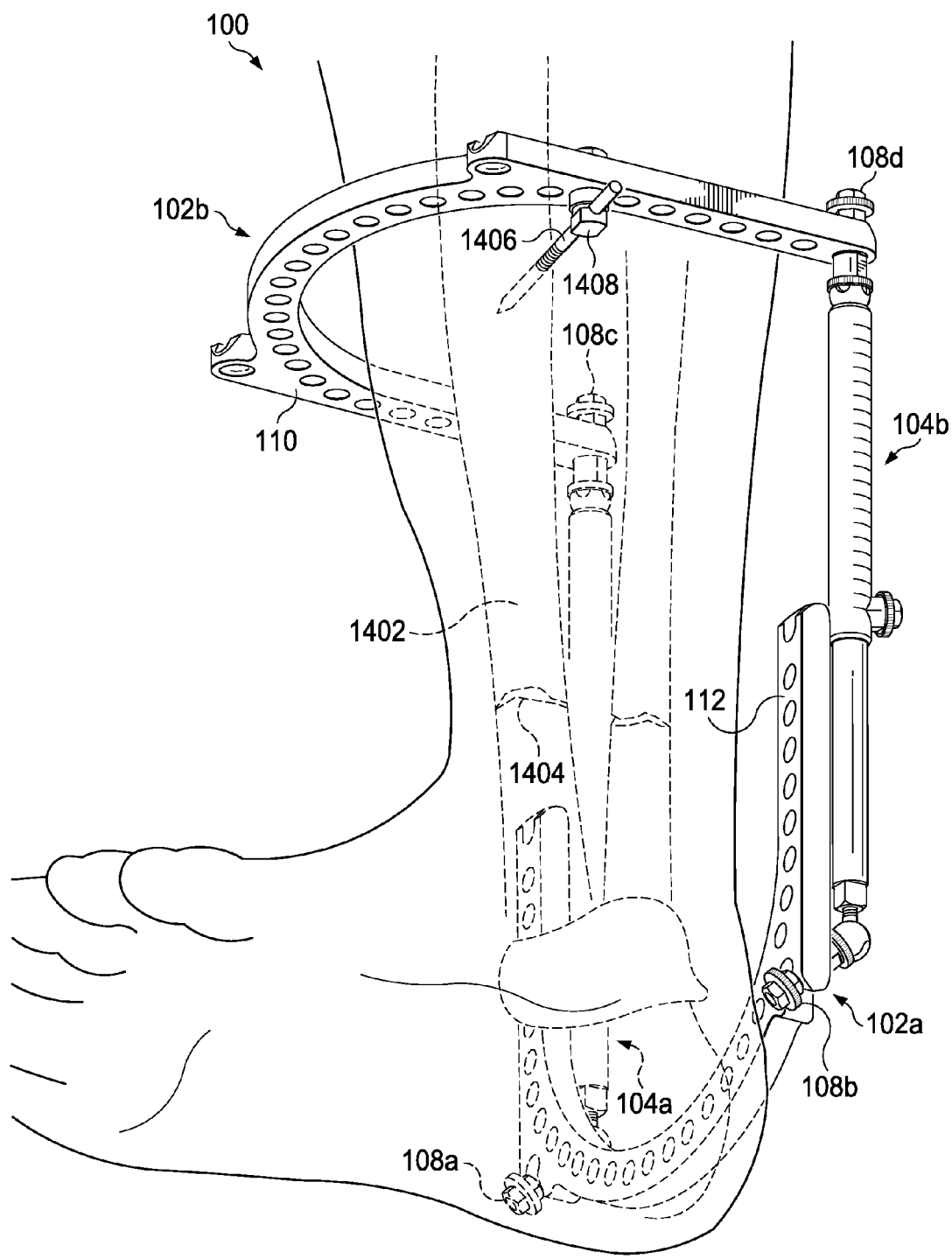
FIG. 14B illustrates an isometric view of a collapsible fixator system that is partially assembled to surround a fractured human tibia bone, in accordance with one embodiment of the present disclosure.
Figure 14C:
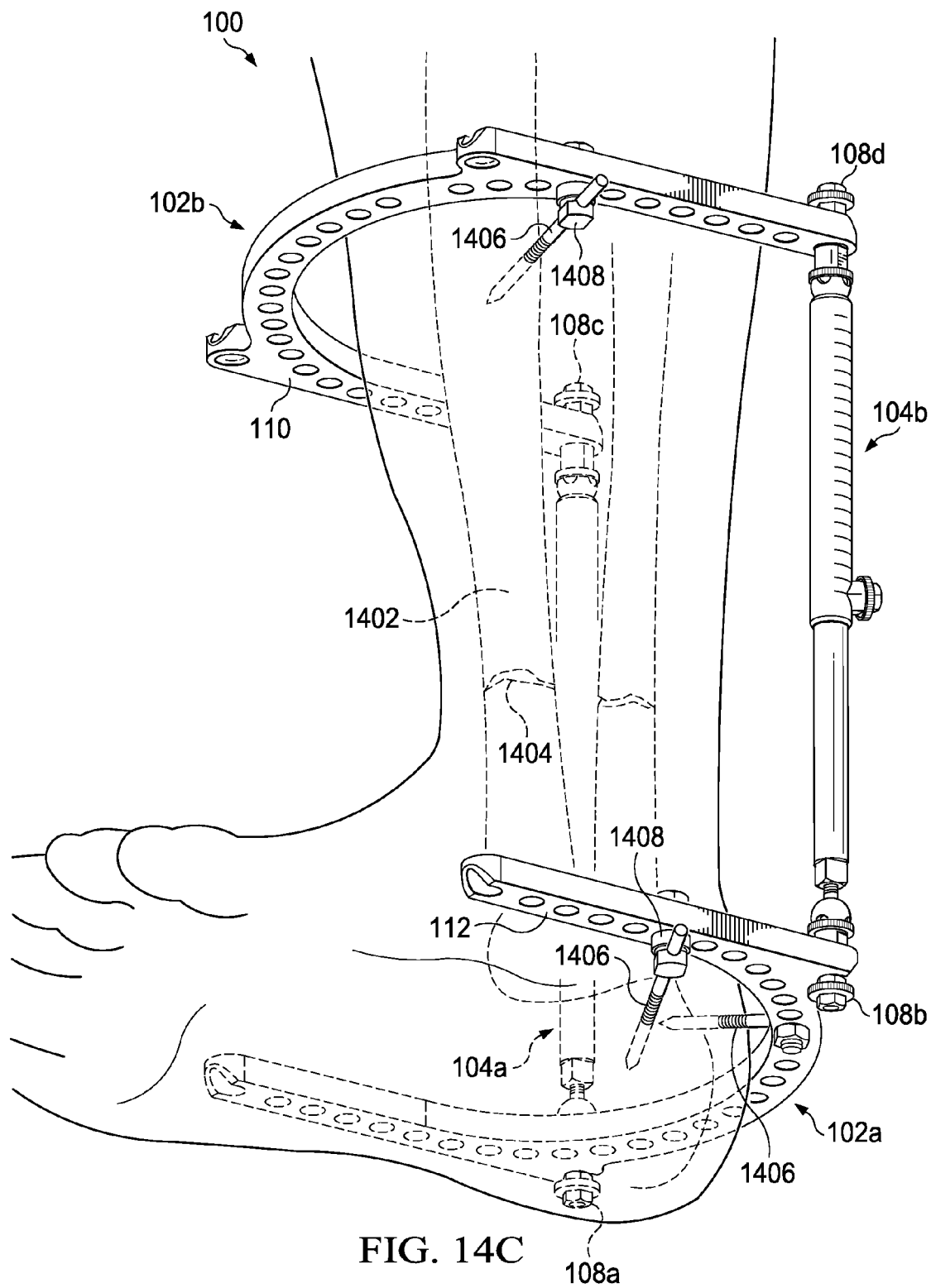
FIG. 14C illustrates an isometric view of the collapsible fixator system of FIG. 14B that is fully assembled to surround a fractured human tibia bone, in accordance with one embodiment of the present disclosure.

FIGS. 14A-14C illustrate example embodiments of employing the collapsible fixator system as described in the present application. FIG. 14A illustrates a frontal view of a fractured human tibia bone. As shown in FIG. 14A, the human tibia bone 1402 may consist of one or more fractures 1404.

FIG. 14B illustrates an isometric view of a collapsible fixator system 100 that is partially assembled to surround a fractured human tibia bone, in accordance with one embodiment of the present disclosure. As shown in FIG. 14B, the collapsible fixation system 100 may be constructed along and at least partially surrounding the human tibia bone 1402 which consists of one or more fractures 1404. The second frame member 102b may be fitted to at least partially surround the human tibia bone 1402. The second strut connector 108d may be positioned with the second strut 104b fixedly positioned substantially perpendicular in relation to the upper surface and the lower surface (not shown) of the second frame member 102b. Likewise, the second strut connector 108c may be positioned with the first strut 104a fixedly positioned substantially perpendicular in relation to the upper surface and the lower surface of the first frame member 102a. The first strut connector 108b may be releasably positioned such that the upper surface 110 and the lower surface 112 of the first frame member 102a are substantially parallel to the second strut 104b. Likewise, the first strut connector 108a may be releasably positioned such that the upper surface 110 and the lower surface 112 of the first frame member 102a are substantially parallel to the first strut 104a.

FIG. 14C illustrates an isometric view of the collapsible fixator system 100 of FIG. 14B that is fully assembled to surround a fractured human tibia bone 1402, in accordance with one embodiment of the present disclosure. As shown in FIG. 14C, the collapsible fixation system 100 may be constructed along and at least partially surrounding the human tibia bone 1402 which consists of one or more fractures 1404. The first frame member 102a and second frame member 102b may be fitted to at least partially surround the human tibia bone 1402 such that the first frame member 102a and second frame member 102b are fixedly spaced apart from one another. The strut connectors 108a, 108b, 108c, and 108d may be positioned with the first strut 104a and the second strut 104b fixedly positioned substantially perpendicular in relation to the upper surfaces 110 and the lower surfaces 112 of the first frame member 102a and the second frame member 102b, thus placing the collapsible fixator system 100 in the second, erect position such that the first frame member 102a and the second frame member 102b are fixedly spaced apart from one another.

In other embodiments, the collapsible fixator system may be placed in the second, erect position such that the first frame member 102a and the second frame member 102b are fixedly spaced apart from one another, without requiring that the first strut 104a and the second strut 104b be positioned substantially perpendicular in relation to the upper surfaces 110 and the lower surfaces 112 of the first frame member 102a and the second frame member 102b (as shown in FIG. 2B).

In an embodiment, one or more pins 1406 may be attached to the collapsible fixation system 100 and connected to the bones near the one or more fractures 1404 that require healing. The pins 1406 may be drilled or pierced through the patient's skin and into the patient's bone for installation of the external fixation device. The pins 1406 may be connected to the first frame member 102a and the second frame member 102b by one or more connection means 1408 at the one or more top holes (as discussed in relation to FIG. 3) or at the one or more side holes (as discussed in relation to FIG. 8). In other embodiments, connection of the collapsible fixation system 100 to the bone(s) may include placing connectors, such as wires, pins, screws, and/or rods, through the skin and into, through, and/or around the selected bone(s).

Figure 15:
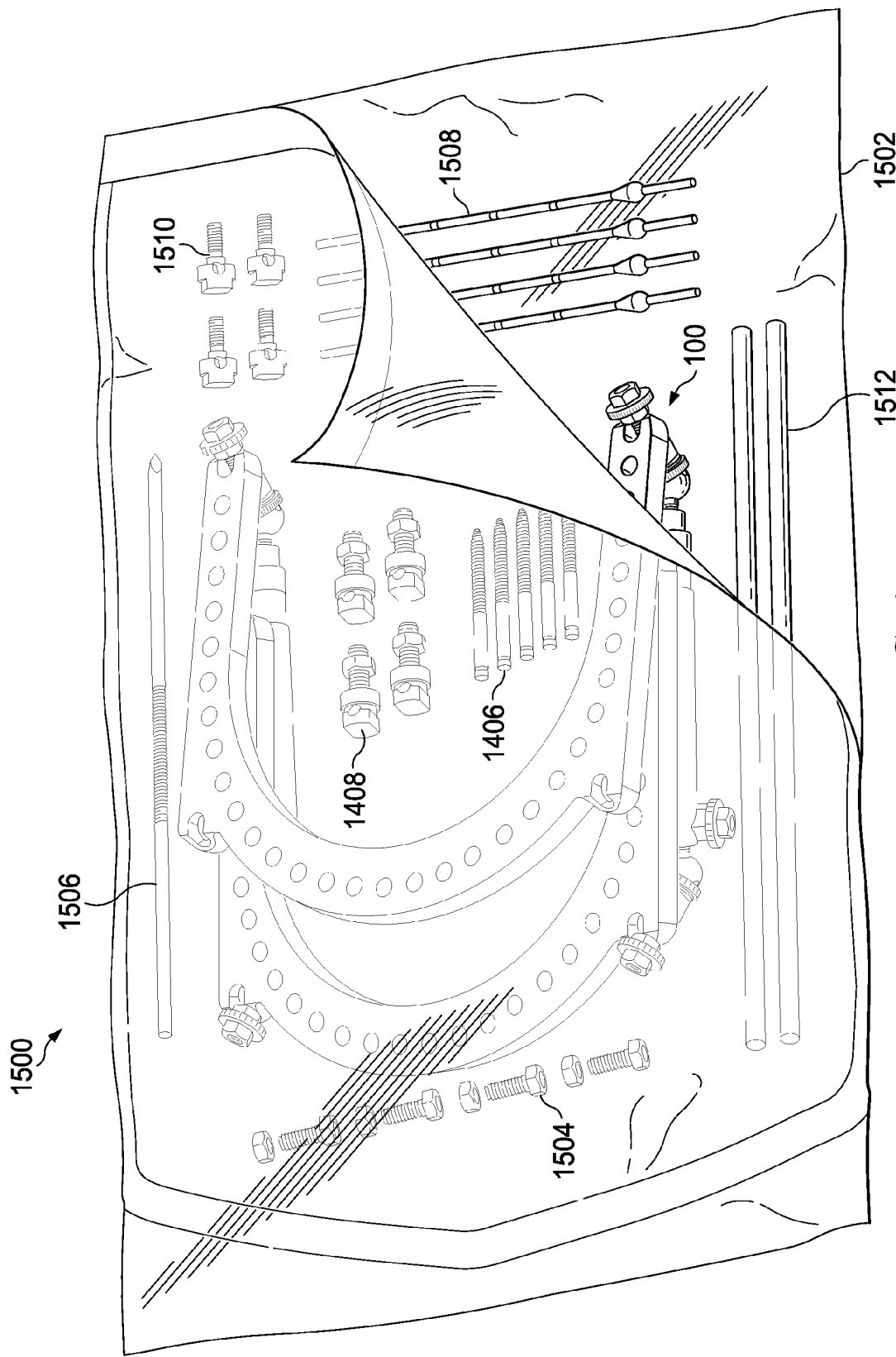
FIG. 15 illustrates an isometric view of a partially opened surgical kit comprising a collapsible fixator system, in accordance with one embodiment of the present disclosure.

FIG. 15 illustrates an isometric view of a partially opened surgical kit 1500 comprising a collapsible fixator system, in accordance with one embodiment of the present disclosure. The surgical kit 1500 may comprise a sterile package 1502 that may be clear on one side to allow a medical professional to easily see what is contained within the sterile package 1502. Within the sterile package 1502, the surgical kit 1500 may comprise a pre-assembled, collapsed collapsible fixation system 100 (as discussed in relation to FIG. 1) and various fixation elements. The fixation elements may include the one or more half pins 1406 and one or more connection means 1408 (as discussed in relation to FIGS. 14B and 14C). Further, the fixation elements may include regular bolts and nuts 1504, one or more centrally threaded full pins 1506, one or more olive wires 1508, one or more fixation bolts 1510, and one or more delivery devices 1512.

It is contemplated that any embodiment discussed in this specification can be implemented with respect to any method, kit, or device of the disclosure, and vice versa. Furthermore, devices taught herein can be used to achieve methods of the disclosure.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A collapsible fixator system comprising:
    a first frame member and a second frame member, each frame member comprising:
        an upper surface;
        a lower surface; and
        a plurality of apertures extending from the upper surface to the lower surface, wherein each of the plurality of apertures comprises an upper portion and a lower portion; and
    at least one strut comprising:
        a first strut connector disposed on a first end of the strut; and
        a second strut connector disposed on a second end of the strut;
        wherein the first strut connector is operable to releasably connect the first end of the strut to the first frame member at a first aperture; and
        wherein the second strut connector is operable to releasably connect the second end of the strut to second frame member at a second aperture;
    wherein when the first and second strut connectors are in a first, collapsed position, the at least one strut is releasably positioned substantially parallel to the upper and lower surfaces of the first and second frame members; and
    wherein when the first and second strut connectors are in a second, erect position, the at least one strut is fixedly positioned such that the first and second frame members are spaced apart from one another.

2. The collapsible fixator system of claim 1, wherein one or more of the upper portions of the apertures comprises a recessed area defined within the upper surface of the frame member and operable to receive a hemispherical feature of a strut.

3. The collapsible fixator system of claim 1, wherein one or more of the lower portions of the apertures comprises a leveled region substantially parallel to and defined within the lower surface of the frame member and operable to interact with the first or the second strut connector.

4. The collapsible fixator system of claim 3, wherein one or more of the lower portions of the apertures further comprise an inclined region operable to interact with the first or the second strut connector.

5. The collapsible fixator system of claim 4, wherein the inclined region gradually slopes from an outer surface of the frame member to the leveled region.

6. The collapsible fixator system of claim 4, wherein when a strut connector is in the first position, the strut connector is adjacent to the inclined region of the aperture.

7. The collapsible fixator system of claim 3, wherein when a strut connector is in the second position, the strut connector is adjacent to the leveled region of the aperture.

8. The collapsible fixator system of claim 1, wherein the at least one strut further comprises a body positioned between the first strut connector and the second strut connector.

9. The collapsible fixator system of claim 8, wherein the at least one strut further comprises a first hemispherical feature positioned between the body and the first strut connector, and a second hemispherical feature positioned between the body and the second strut connector.

10. The collapsible fixator system of claim 9, wherein the first hemispherical feature is operable to rotate within an upper portion of the first aperture such that the first strut connector reversibly transitions between the first and second positions, and wherein the second hemispherical feature is operable to rotate within an upper portion of the second aperture such that the second strut connector reversibly transitions between the first and second positions.

11. The collapsible fixator system of claim 9, wherein the at least one strut further comprises a first rotational joint member positioned between the body and the first strut connector, and a second rotational joint member positioned between the body and the second strut connector.

12. The collapsible fixator system of claim 11, wherein the first rotational joint member is operable to rotate the first strut connector and the body relative to one another, and wherein the second rotational joint member is operable to rotate the second strut connector and the body relative to one another.

13. The collapsible fixator system of claim 1, wherein each of the first frame member and the second frame member are substantially U-shaped comprising a first arm, a second arm, and a connecting portion defined there between.

14. The collapsible fixator system of claim 13, wherein each of the first frame member and the second frame member further comprises a first protruding portion and a second protruding portion,
wherein the first protruding portion is proximate to the first arm and the connecting portion, and
wherein the second protruding portion is proximate to the second arm and the connecting portion.

15. The collapsible fixator system of claim 14,
wherein the plurality of apertures comprises a first aperture, a second aperture, a third aperture, and a fourth aperture,
wherein the first aperture is defined between the upper and lower surfaces at an end of the first arm,
wherein the second aperture is disposed at the first protruding portion,
wherein the third aperture is disposed at the second protruding portion, and wherein the fourth aperture is defined between the upper and lower surfaces at an end of the second arm.

16. The collapsible fixator system of claim 15,
wherein an upper portion of the third aperture of the first frame member is operable to receive a first end of the first strut,
wherein an upper portion of the fourth aperture of the second frame member is operable to receive a second end of the first strut,
wherein an upper portion of the second aperture of the first frame member is operable to receive a first end of the second strut, and wherein an upper portion of the first aperture of the second frame member is operable to receive a second end of the second strut.

17. A method of collapsing or erecting a fixator system comprising:
providing a first frame member and a second frame member, each frame member comprising:
an upper surface;
a lower surface; and
a plurality of apertures extending from the upper surface to the lower surface, wherein each of the plurality of apertures comprises an upper portion and a lower portion; and
providing at least one strut comprising:
a first strut connector disposed on a first end of the strut; and
a second strut connector disposed on a second end of the strut;
releasably connecting the first strut connector to the first frame member through a first aperture;
releasably connecting the second strut connector to the second frame member through a second aperture; and
transitioning the first and second strut connectors between a first, collapsed position and a second, erect position,
wherein when the first and second strut connectors are in the first, collapsed position, the at least one strut is releasably positioned substantially parallel to the upper and lower surfaces of the first and second frame members; and
wherein when the first and second strut connectors are in a second, erect position, the at least one strut is fixedly positioned such thatthe first and second frame members are spaced apart from one another.

18. The method of claim 17, wherein the upper portion comprises a recessed area defined within the upper surface of the frame member and operable to receive a hemispherical feature of a strut.

19. The method of claim 17, wherein the lower portion comprises a leveled region substantially parallel to and defined within the lower surface of the frame member and operable to interact with the first or the second strut connector.

20. The method of claim 19, wherein the lower portion further comprises an inclined region operable to interact with the first or the second strut connector.

21. The method of claim 20, wherein the inclined region gradually slopes from an outer surface of the frame member to the leveled region.

22. The method of claim 20, wherein when a strut connector is in the first position, the strut connector is adjacent to the inclined region of the aperture.

23. The method of claim 19, wherein when a strut connector is in the second position, the strut connector is adjacent to the leveled region of the aperture.

24. A surgical kit comprising:
a sterile package;
a pre-assembled collapsible fixator system comprising:
a first frame member and a second frame member, each frame member comprising:
an upper surface;
a lower surface; and
a plurality of apertures extending from the upper surface to the lower surface, wherein each of the plurality of apertures comprises an upper portion and a lower portion; and at least one strut comprising:
a first strut connector disposed on a first end of the strut; and
a second strut connector disposed on a second end of the strut;
wherein the first strut connector is operable to releasably connect the first end of the strut to the first frame member at a first aperture; and
wherein the second strut connector is operable to releasably connect the second end of the strut to second frame member at a second aperture;
wherein the first and second strut connectors are in a first, collapsed position, and the at least one strut is releasably positioned substantially parallel to the upper and lower surfaces of the first and second frame members; and a plurality of fixation elements.

* * * * *